(12) United States Patent
López Más et al.

(10) Patent No.: US 8,236,993 B2
(45) Date of Patent: Aug. 7, 2012

(54) PROCESS AND APPARATUS FOR THE PRODUCTION OF HYDROXYTYROSOL CONTAINING EXTRACT FROM OLIVES AND SOLIDS CONTAINING RESIDUES OF OLIVE OIL EXTRACTION

(75) Inventors: José A. López Más, Alhama de Murcia (ES); Sergio A. Streitenberger, Murcia (ES); Marcos Peñalver Mellado, Murcia (ES); Pedro Martinez Ortiz, Murcia (ES)

(73) Assignee: Probelte Pharma, S.A., Espinardo Murcia (ES)

( * ) Notice: Subject to any disclaimer, the term of this patent is extended or adjusted under 35 U.S.C. 154(b) by 239 days.

(21) Appl. No.: 12/524,603

(22) PCT Filed: Jan. 25, 2008

(86) PCT No.: PCT/IB2008/000173
§ 371 (c)(1),
(2), (4) Date: Dec. 15, 2009

(87) PCT Pub. No.: WO2008/090460
PCT Pub. Date: Jul. 31, 2008

(65) Prior Publication Data
US 2010/0160690 A1  Jun. 24, 2010

(30) Foreign Application Priority Data
Jan. 26, 2007 (EP) .................................... 07001791
Jul. 23, 2007 (EP) .................................... 07014390

(51) Int. Cl.
*C07C 37/68* (2006.01)
*A23L 1/00* (2006.01)

(52) U.S. Cl. .......................... 568/753; 568/750; 426/431
(58) Field of Classification Search .................. 568/753
See application file for complete search history.

(56) References Cited

U.S. PATENT DOCUMENTS

| 6,361,803 | B1 | 3/2002 | Cuomo et al. |
| 6,849,770 | B2 * | 2/2005 | Guzman et al. ............... 568/763 |
| 2004/0102657 | A1 | 5/2004 | Fernandez-Bolanos Guzman et al. |
| 2004/0176647 | A1 | 9/2004 | Perdices et al. |

FOREIGN PATENT DOCUMENTS

| EP | 1 582 512 A1 | 10/2005 |
| EP | 1 623 960 A1 | 2/2006 |
| WO | WO 2004/005228 A1 | 1/2004 |

OTHER PUBLICATIONS

Database CAPLUS on STN, Acc. No. 2004:143424, Fernandez-Bolanos Guzman, ES 2172429 A1 (Sep. 16, 2002) (abstract).*
International Search Report for PCT International Application No. PCT/IB2008/000173 mailed May 23, 2008.

* cited by examiner

*Primary Examiner* — Brian J Davis
(74) *Attorney, Agent, or Firm* — RatnerPrestia

(57) ABSTRACT

Hydroxytyrosol is extracted from olives and/or from the solid residues of olives after the extraction of olive oil, by carrying out acid hydrolysis at a temperature within the range of 110° C. to 140° C. and at a pH within the range of 1.0 to 6.0, and by purifying the obtained solution on a column containing acid activated anion exchange resins, and a column containing an adsorbent non-ionic resin; both columns being eluted with water to recover the hydroxytyrosol.

13 Claims, 2 Drawing Sheets

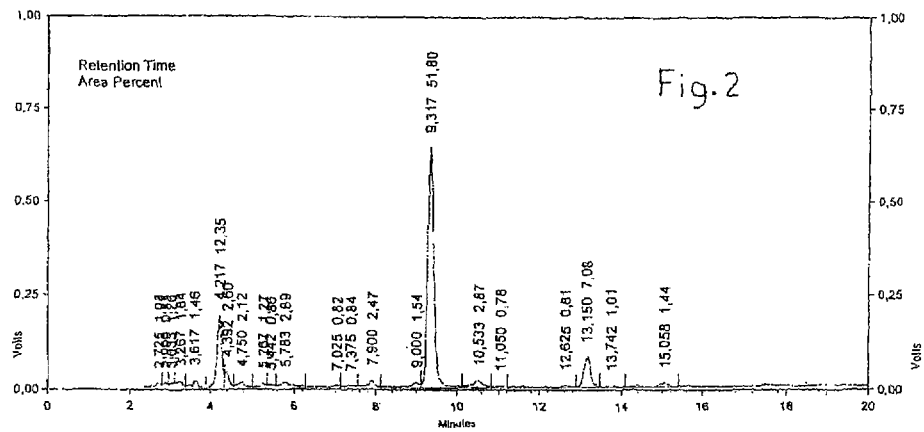
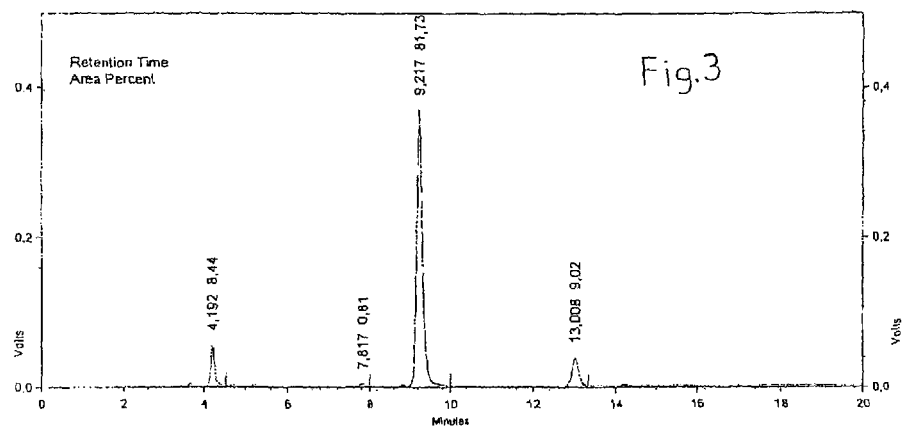
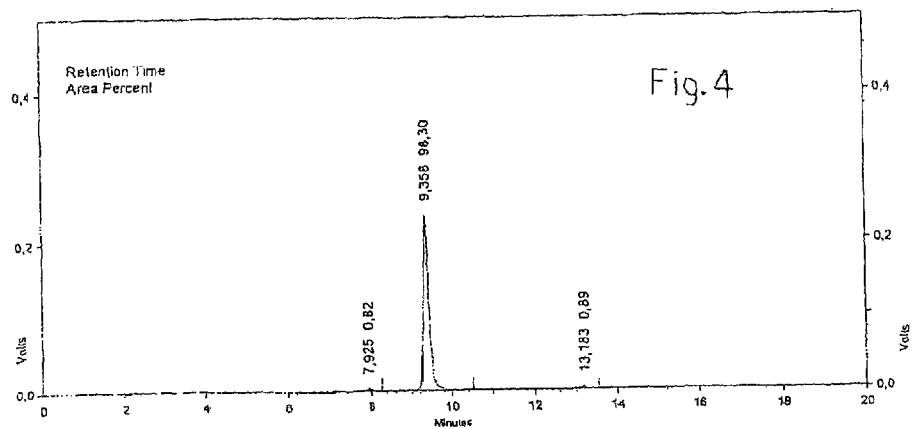

PROCESS AND APPARATUS FOR THE PRODUCTION OF HYDROXYTYROSOL CONTAINING EXTRACT FROM OLIVES AND SOLIDS CONTAINING RESIDUES OF OLIVE OIL EXTRACTION

This application is a U.S. National Phase Application of PCT International Application No. PCT/IB2008-000173, filed Jan. 25, 2008.

FIELD OF THE INVENTION

The present invention relates to a process and an apparatus for the production of hydroxytyrosol containing extract from olives and/or the solid-containing residues of olives after the extraction of olive oil. More particularly, the invention relates to the production of hydroxytyrosol-containing extracts to be used as a source of hydroxytyrosol in food, medical and cosmetic industries.

BACKGROUND OF THE INVENTION

It is now well known that olives contain a number of bioactive compounds, particularly polyphenols; among these polyphenols, hydroxytyrosol is of outstanding biological significance in view of its antioxidant, antimicrobial and radical scavenging activity.

Hydroxytyrosol has the following formula:

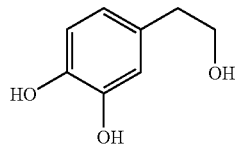

Production of hydroxytyrosol from olives residues after oil extraction was and is actively investigated; an efficient extraction process could be very profitable especially because the major amount of hydroxytyrosol and hydroxytyrosol precursors initially present in the olives remains in the residues from olive oil production and only a minor part is found in the oil. Extra virgin olive oil normally contains 1-20 ppm of hydroxytyrosol.

The residues of olive oil extraction of interest for the present application exclude the olive tree leaves, because the leaves are removed before oil extraction. Moreover, hydroxytyrosol extraction from leaves faces different starting compositions (and therefore different extraction problems) than extraction from olives or olive residues.

The residues of olives as obtained from olive oil extraction processes of interest for the present application can be classified as:

pomaces, i.e. the solids containing residues of the pressing (in spanish: orujo), of the three-phases process (orujo), or of the two-phases process, in which no water is added to the chopped olives in the centrifugation step (in spanish: alperujo). Orujo, alperujo and defatted orujo contain a high amount of water (45% to 70%). Extraction residues also comprise orujillo, the olive dry solids, after orujo oil extraction that contains less than 15% water and is nearly free from oil residues.

The green olives extracts of the invention are preferred to the extracts of residues of olive oil production in view of their greater amount of hydroxytyrosol and of the reduced content of hydroxymethylfurfural.

For the purposes of the present description the term "pomaces" or "solid residue" is designating both "orujo", "defatted orujo" "orujillo" and "alperujo". Preferred starting materials for the present invention are olives, more preferably green olives, and pomaces.

It is known to carry out acid hydrolysis of the pomaces (or of vegetation water) to have the cleavage of the ester bond in the oleuropein molecule and obtain hydroxytyrosol.

U.S. Pat. No. 6,361,803 discloses extraction of hydroxytyrosol (and other compounds) by neutral or acid hydrolysis of olive pulp residues at reflux for one hour (ex. 12). The extracted water solution is loaded on an absorption XAD-7 column that is eluted with methanol to recover the extracted hydroxytyrosol. U.S. Pat. No. 6,361,803 requires the use of organic polar solvents, to recover hydroxytyrosol with a minimum purity grade, in addition (ex. 12) freeze precipitation of some impurities from the methanol solution is necessary. Polar aqueous solvents are selected among methanol, ethanol, acetonitrile or acetone, while polar organic solvents are selected, for example, among esters, amides, dimethyl sulfoxide, dioxane, DMF and their mixtures. Most of these solvents are toxic and very difficult to completely eliminate from the desired hydroxytyrosol product. Accordingly, traces of the utilized solvents will be found in the final product even after several purification steps, thus rendering the hydroxytyrosol obtained according to this process not suitable for a safe application in the alimentary, cosmetic and pharmaceutical field. Moreover, the final product is not suitable for use in fortifying foods, particularly edible oils, without use of ethanol and acetic acid as additives to the extract to obtain a stable food product: the resulting food product (oil plus hydroxytyrosol containing extract, ethanol and acetic acid) is not acceptable in the food industry.

WO 2004/005228 discloses hydrolysis at room temperature of vegetation water obtained from olive oil extraction by incubation of the acidified vegetation water for at least two months and preferably 6-12 months until at least the 50% (preferably 90%) of the oleuropein originally present in the vegetation water has been converted to hydroxytyrosol. The incubated vegetation water is extracted with an organic solvent, for example ethyl acetate, or it is contacted with a supercritical fluid ($CO_2$), to produce a rich fraction in hydroxytyrosol. The main problems of this process are the very long time required for the incubation of the acidified vegetation water and the use of organic solvents, that should be avoided, particularly when the final product obtained is to be used in the alimentary, cosmetic and pharmaceutical field.

US 2004/0102657 discloses acidic hydrolysis with a steam explosion process at high temperatures (about 190-220° C.). The obtained solution is firstly partially purified on a column with non activated ion exchange resin and subsequently loaded on a XAD non-ionic column, from where the hydroxytyrosol is eluted with methanol or ethanol. The process results in a poor yield in hydroxytyrosol, considering the process in its entirety.

EP 1623960 discloses a process of recovery of hydroxytyrosol, and tyrosol, from alpechin by means of filtration in a complicated plant consisting of three units (Ex. 1) and subsequent separation. The tyrosol is then oxidated to hydroxytyrosol in a protic solvent (alcohol or water) to obtain a final product that is semi-synthetic. Additionally, EP 1623960 discloses that concentration by nanofiltration and reverse osmosis of vegetation waters (alpechin) are carried out at neutral or alkaline pH (claim 4). This process has two important problems. A first drawback is that hydroxytyrosol degradation increases at neutral and alkaline conditions appearing unwanted products that are difficult to remove, and, in addition, due to the fact that no acid hydrolysis is carried out the oleuropein content should be still high. Secondly, the obtainable concentration factor is poor, thus the maximum concentration allowed for hydroxytyrosol according Ex-1 (see table 1) is in the range from 1.2 to 1.6 g/L.

US 2004/0176647 discloses an extraction process of phenols from alperujo under stirring at 180-240° C. in autoclave, in water. No acid is added, but the thermal treatment results in a "liberation of acetyl groups" and in an alleged consequent reduction of the pH (page 3, first paragraph). Nevertheless, at the pHs produced in the described conditions hydrolysis of oleuropein is far to be complete, meaning two tings, lower hydroxytyrosol yields and remaining hydrolysed oleuropein, that as we discuss above is associated causing non-pleasant taste in food products containing such extracts, being then not suitable for food applications. The products are tyrosol and hydroxytyrosol, that are separated by HPLC with sulphuric acid/acetonitrile eluent.

Summarizing, the above mentioned techniques are either too long or too complex, or too harsh, or all of the above; this results in that the amount of remaining oleuropein, i.e. the amount that is not hydrolyzed, and/or the amount of the hydrolysis by-products such as hydroxymethylfurfural is high enough to make difficult the subsequent purification steps.

SUMMARY OF THE INVENTION

In fact, the applicant found that generation of by-products is a much bigger problem in the production of hydroxytyrosol extracts than it was previously thought, as it appears from the above discussed prior art documents: the starting materials, especially olives and pomaces, contain inter alia a high amount of phenolic compounds in the form of glucoside and/or its esters including oleuropein, ligustroside, verbascoside and several flavonoids. Several other natural compounds are present, It is very easy to degrade the starting compounds into a plethora of by-products.

As by-products must be eliminated to purify hydroxytyrosol, in the known art the use of organic solvents is required in order to purify the hydroxytyrosol during the subsequent purification steps on chromatographic columns. The use of organic solvents, for example methanol, when eluting from a resin column, is inconvenient, particularly when the final product obtained is to be used in the alimentary, cosmetic and pharmaceutical field.

Moreover, the known hydroxytyrosol rich extracts are not suitable to be used as additives for foods, especially edible oils.

Therefore, there is the need for a process of producing a hydroxytyrosol containing extract that is rich in hydroxytyrosol and has low content of starting products such as oleuropein and verbascosides, and of by-products, particularly hydroxymethylfurfural and in general has a very low content in sugars and in salts.

It is an aim of the present invention to solve the above mentioned problems and to provide a process of producing hydroxytyrosol from olives and/or olive oil extraction by-products that is simple, effective, not expensive and that gives a high purity product free from organic solvents and suitable for use as additive for food, cosmetics etcetera.

Such aim is achieved by means of the present invention that provides a process according to claim 1.

This process entails the acidic hydrolysis in water of the starting materials at a temperature not exceeding 140° C., preferably within the range from 70° C. to 130° C. and most preferably above the reflux temperature, in the range of 110° C. to 130° C. and in a pressurized condition, e.g. in an continuous sterilization system, at a pressure within the range of 10 to 20 psi above the atmospheric pressure. The pH of the acidified mixture that undergoes the hydrolysis is within the range of 1.0 to 6.0. The mixture after the hydrolysis is clarified by physical methods known in the art, e.g. by filtering and/or centrifuging, to remove the suspended solids from the hydrolysis water solution, and to obtain a clarified solution substantially free of solids in suspension.

The starting materials are olives or pomaces, i.e. the above defined residues from olive oil extraction. Preferred olives are green olives, pomaces are preferably free from oil. Oil is removed either before or after the hydrolysis step by means known in the art (e.g. those used to prepare defatted orujo or orujillo) or by use of diatomaceous earth or other filter means.

According to the invention the above steps (acid hydrolysis and clarification) are followed by the steps of loading the product thus obtained in at least one chromatographic column of an acid activated anion exchange resin, and of eluting the products retained in said chromatographic column with water.

In a preferred aspect, the invention provides for a further purification step carried out by loading the water-eluted solution from the first column (anion exchange) in at least one chromatographic column of adsorbent non-ionic resins and of eluting the products retained in said second chromatographic column with water.

According to a further aspect of the invention the liquid product is concentrated e.g. by reverse osmosis concentration. According to a further step, after chromatographic purification and reverse osmosis concentration, the resulting liquid product is brought to a solid form, e.g. by freeze-drying, vacuum rotaevaporation or spray drying, with or without carriers such as maltodextrines.

A further object of the inventions are the hydroxytyrosol containing extracts as obtainable according to the above mentioned process. These extracts may be either in liquid or solid form and are characterized by having a hydroxytyrosol content of at least 0.5% (w/w) and a purity of at least 40% and preferably of at least 80% and more preferably of at least 95% (as determined by HPLC peak area measured at 280 nm). These extracts are free from organic solvents, from hydroxymethylfurfural and also substantially free from sugars and salts. According to a preferred aspect of the invention, the hydroxytyrosol containing liquid product obtainable according to the invention, has a hydroxytyrosol content of at least 35% (w/w) or even more preferably of at least 45% (w/w), a purity of at least 90% (by HPLC 280 nm) and a total phenols content of at least 35%. According to a more preferred aspect of the invention, the hydroxytyrosol containing solid product obtainable according to the invention, has a hydroxytyrosol content of at least 20% (w/w), a purity of at least 90% (by HPLC 280 nm) and a total phenols content of at least 20%.

According to a preferred aspect of the invention, the hydroxytyrosol containing solid product obtainable according to the invention, has a hydroxytyrosol content of at least 90% (w/w), a purity of at least 90% (by HPLC 280 nm) and a total phenols content of at least 92%.

A further object of the invention is an apparatus for carrying out the process as above discussed, characterized according to claim 13.

According to the invention, the apparatus, or plant, comprises a reactor for carrying out acidic hydrolysis under pressure and at least one chromatographic column containing a resin acid activated anion exchange resin that is a weakly basic, water elutable anion exchange resin and at least one chromatographic column containing an adsorbent non-ionic resin that is a macroreticular cross-linked aromatic polymer resin.

The invention provides several advantages over the prior art techniques.

First of all, the hydrolysis step is carried out, according to the present invention, using just water and mineral acid, keeping the temperature in the claimed range above the reflux temperature using a combination of heating and pressure. When pressure is applied together with the claimed heating temperature, the resulting hydrolysis reaction is almost completed in about half an hour, without significant formation of by-products and with a very good conversion of the starting material (oleuropein) into the final desired product (hydroxytyrosol). The hydrolysis step according to the present invention allows to obtain, in a short time, a very good yield in hydroxytyrosol together with a quite complete absence of those by-products, that are difficult to eliminate and which are instead formed, according to the prior art, in significant amounts.

The hydrolysis step, carried out according to the invention, provides for another advantage. The combined use of acids and temperature, beside its main objective, that is to carry out the hydrolysis with a good conversion rate and avoiding the formation of detrimental by-products, results in a sterilization of the mixture. In fact, the hydrolysis step provides a sterilization of the water solution, i.e. of the products involved, that is very useful, as the starting material (for example pomaces) used in the processes for the preparation of hydroxytyrosol, usually comes from already treated materials, and generally requires some depuration-sterilization pre-treatments, to give a safe hydroxytyrosol final product. Said depuration-sterilization pre-treatments are often complex treatments and require additional process steps that, at the end of the full process, result in a lower yield in the desired final product. According to the present invention, the hydrolysis step contemporaneously allows to carry out the hydrolysis reaction and provides for the necessary sterilization of the products involved, thus avoiding the necessity to carry out any sterilization step on the starting material as well as providing for a hydrolysed material that is ready for further uses, without any additional sterilization treatment.

In addition, the hydrolysis step is followed by at least a purification step, which is carried out by loading the product obtained from the hydrolysis step in at least a single chromatography column system or in a two chromatography columns system and eluting the hydroxytyrosol retained in said chromatographic columns with water. In this case, as there are very low amounts of by-products coming from the hydrolysis step, it is possible to make use of a chromatographic column that can be eluted with water in the absence of any organic solvent, either alone or mixed with water. This means that no organic solvents are contacted with the hydroxytyrosol, thus obtaining a purified hydroxytyrosol that is particularly suitable to be used in the alimentary, cosmetic and pharmaceutical field.

Another advantage of the present invention is due to the concentration step, that allows to enrich the hydroxytyrosol content after the purification steps. These purification steps produce a liquid extract, substantially free from sugars and salts, resulting in a very important reduction of the osmotic pressure during the concentration step of the purified liquid extract permitting thus a very high concentration factor (until 350 times). This concentration step provides a "concentrate" characterized by a high content of hydroxytyrosol, which can be directly used for further treatments. According to the prior art, where no "concentration" steps are usually provided or when provided they have poor concentration factors (about 2 to 5 times) due to the lack of a previous purification that removes sugars and salts, in the described processes for hydroxytyrosol preparation, the hydroxytyrosol concentration in the processed solutions/dispersions is always very low, thus resulting in the necessity to operate with great volumes with consequent lower yields in the final product.

Always according to the present invention, the possibility to obtain a solid final product that is not mixed with any carrier, for example maltodextrines, gives the opportunity to formulate purified hydroxytyrosol according to its final intended use and according to any formal requirement, possibly required.

BRIEF DESCRIPTION OF THE DRAWINGS

The invention will now be further disclosed in greater detail with reference to the enclosed non-limiting drawings wherein:

FIGS. 2-4 are chromatograms of three hydroxytyrosol containing products according to three embodiments of the invention process.

DESCRIPTION OF PREFERRED EMBODIMENTS

Figure 1:
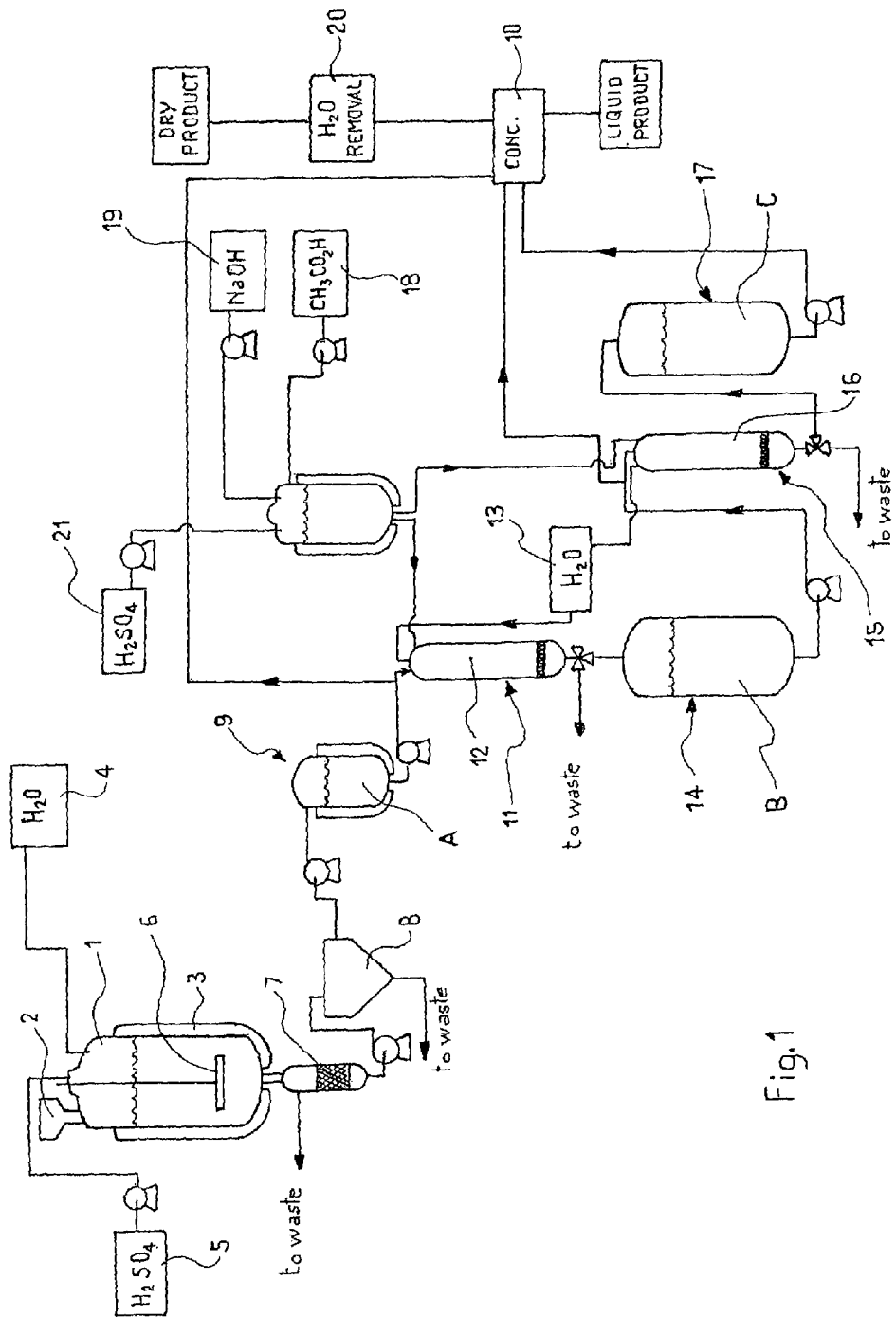
FIG. 1 is a schematic view of an apparatus according to the invention.

With reference to FIG. 1, the invention apparatus comprises a means, or reactor, 1, preferably a continuous sterilization system, in which the hydrolysis according to the invention process is carried out.

As previously mentioned, the hydrolysis is carried out at a temperature that does not exceed 140° C., in a reactor. Preferably the temperature range is 70 to 130° C. and most preferably it is above reflux temperature, in a range 110 to 130° C., at a pressure of 10 to 20 psi above the atmospheric pressure and for a time length within the range of 15 to 45 minutes. Preferably, the hydrolysis temperature is within the range of 118 to 126° C. and in the most preferred embodiment the hydrolysis is carried out at 120-121° C., at 15 psi (over the atmospheric pressure) for 30 minutes. A preferred reactor is a continuous sterilization system.

The continuous sterilization system 1 is provided with feeding means 2 for feeding to it the starting materials, namely the residues, or by-products, of olive oil extraction, namely pomaces (i.e. the solid residues of the pressed olives). Continuous sterilization system 1 is suitable to treat the starting materials in a continuous process rather than batchwise. Heating means 3 for heating the reactor 1 to the above mentioned temperatures are provided in a known way, e.g. as a jacket around the reactor. Reactor 1 is also provided with a supply of demineralised water 4 and with means 6 to stir the water mixture of starting product. Usually, the ratio water to solids is within the range of 1:1 to 4:1

The hydrolysis process is carried out at a pH of 1.0 to 6.0, preferably of 1.0 to 3.0. The required amount of acid, preferably sulphuric acid, is obtained from acid tank 5.

The combination of acidic conditions and of temperature in the claimed ranges results in a hydrolysis process that is fast and efficient and can last for 30 minutes only, at 120-123° C. and a pressure of 15 psi above the atmospheric pressure. Moreover, the process also results in the sterilization of the hydrolysis products.

The outlet of continuous sterilization system, i.e. reactor, 1 is connected with a filter 7 for removing solids from the reaction mixture containing hydroxytyrosol and other phenols. The filtered portion is then sent to a further separation means, preferably a centrifuge 8, where further solids are removed from the reaction mixture to obtain a liquid substantially free from suspended solids, i.e. a solution that is suitable for the following purification. The clarified liquid after centrifugation has a brownish colour and is preferably stored in reservoir 9. The clarified liquid A is now containing hydroxytyrosol, a residue of oleuropein and minor amounts of phenols and other products. FIG. 2 chromatogram shows the composition and the percent of the detected compounds in this liquid and is obtained by HPLC at 280 nm; the major peak at 9.317 minutes is hydroxytyrosol and the peak at 13.150 minutes is tyrosol.

According to a preferred embodiment of the invention, liquid A is concentrated by evaporation or tangential flow filtration (TFF), (e.g. by using a reverse osmosis system). The concentration step can be carried out on liquid A directly or, preferably, after a purification step by means of at least one chromatographic column. To this end, storage tank, or reservoir, 9 is connected with means of concentrating 10, e.g. by TFF or preferably by reverse osmosis, and to purification means.

Purification means comprises in one embodiment a single column system comprising a chromatographic column of a resin selected from acid activated anion exchange resins. In another preferred embodiment purification means comprises, in addition to the above mentioned first column of acid activated anion exchange resins at least a further, second, chromatographic column of a resin selected from adsorbent non-ionic resins.

In another more preferred embodiment, the acid activated anion exchange resin is a weakly basic anion exchange resin, and the adsorbent non-ionic resin is a macroreticular cross-linked aromatic polymer.

The anion exchange resins used as a chromatographic resin for the purification of hydroxytyrosol of the present invention are not particularly limited so long as they can be acid activated. Examples of preferred weakly basic anion exchange resins include polyamine-type resins (including polyamine-type chelating resins) such as reaction products of a styrene/divinylbenzene copolymer and diethylenetriamine or other, and resins as polymerization products of compounds mainly comprising allylamine, vinylamine or other; and acrylic resins such as copolymers of divinylbenzene and amide compounds which comprise acrylic acid or methacrylic acid and dimethylaminopropylamine or other. Other resins may also be used in which the aforementioned weakly basic anion exchange resin is partly substituted with strongly basic exchange groups such as trimethylamine, dimethylethanolamine or other. More specifically, known in the art resins which have been used so far can be used, for example, Diaion WA10, WA20, WA21 and WA30 (Mitsubishi Chemical), Amberlite IRA-35, IRA-67 (IRA-68), IRA-93ZU, IRA-94S, IRA-478 (Rhöm & Haas), WGR-2 (Dow Chemical) and other.

According to the invention process, these resins are acid activated before being used, preferably with acetic acid. These resins are particularly suitable for the invention process in view of their low cost and of the fact that they can be regenerated in mild conditions. Additionally, the weakly basic nature of the resin allows the partial separation of hydroxytyrosol and tyrosol molecules. From the comparison of the peak ratio hydroxytyrosol/tyrosol and the HPLC purity of the hydroxytyrosol peak of FIGS. 2 and 3, it can be appreciated the efficiency of the chromatographic separation according to the invention.

In fact, the use of a weakly anionic exchange resin allows to separate very similar compounds during the elution, this is not possible by the prior art techniques using strong anionic exchange resins, because the elution of such resins is generally an all-or-nothing process. As previously mentioned, a further advantage is that the retained products can be eluted with water, without using any polar solvent such as methanol.

Suitable adsorption resins are based on non-ionic, hydrophobic, macroreticular cross-linked aromatic polymer. Such resins are typically aromatic polymers, such as styrene and divinylbenzene copolymers, which may be cross-linked. Such resins are known and are generally prepared by polymerization of the appropriate monomers. The adsorption resins used as a chromatographic resin for the purification of hydroxytyrosol of the present invention are not particularly limited so long as they can be water eluted. Examples of preferred adsorption resins, include: Amberlite® XAD-4, XAD-7, XAD-1180, XAD-16 and XAD-1600 (available from Rohm & Haas); XUS-40323.00, XUS-40285.00 and XUS-40283.00 (available from Dow Chemical Co.); and SP-700, SP-825, SP850, Diaion HP 10, HP 20, HP 30, HP 40 and HP 50 (available from Mitsubishi Chemical).

These type of resins are particularly suitable for the invention process in view of their very high adsorption capacity for hydroxytyrosol and of the fact that, thanks to the low content of by-products in the solution obtained after hydrolysis, the adsorbed hydroxytyrosol can be recovered by elution with water, only, without any polar solvent such as methanol or ethanol, as was instead required by the prior art techniques. Adsorbed hydroxytyrosol is recovered substantially quantitatively.

In the shown preferred embodiment, the process of the invention provides for a two-step purification on chromatographic columns.

Liquid A, as obtained from the initial steps a) and b), i.e. hydrolysis and solid separation, is charged into column 11, containing the anion exchange resin 12 as above detailed. The permeate is sent to waste treatment (not shown). Demineralized water from water supply 13 is then fed to column 11 to elute the retained products and the eluted liquid is collected in reservoir 14. The thus obtained liquid product (liquid B) has a purity in hydroxytyrosol of at least 75%, and generally of at least 80%, the purity being determined as the % of the peak areas in a chromatogram by HPLC at 280 nm. The recovery of retained hydroxytyrosol from the resin is at least 85% and is generally at least 90%.

FIG. 3 shows the relevant HPLC chromatogram of the obtained purified liquid product B.

In the second purification step, liquid product B is charged into column 15, containing a non-ionic adsorption resin 16, as above detailed. The permeate is sent to waste treatment and the adsorbed hydroxytyrosol is recovered by elution with demineralized water from supply 13 and is collected in reservoir 17.

Liquid C, i.e. the liquid collected in reservoir 17 has a purity in hydroxytyrosol of at least 90%, and generally of at least 95%, the purity being determined as the percent of the peak areas in a chromatogram by HPLC at 280 nm. The recovery of retained hydroxytyrosol from the resin is at least 90% and is generally at least 95% and substantially quantitative. FIG. 4 shows the relevant HPLC chromatogram of the obtained purified liquid product C.

FIG. 1 also shows a source of acetic acid 18 that is connected to column 11 for acid activation of resin 12 and a source of NaOH 19 or other suitable base for regeneration of the same. Additionally, a source of NaOH 19 for regeneration of resin 16 is connected to column 15 and a source of sulphuric acid 21 for resin surface activation is also shown.

As for liquid A, also liquid B and liquid C can be concentrated in concentration means 10, e.g. by evaporation or TFF, preferably by reverse osmosis; concentration is preferably carried out on liquids B and C, preferably liquid C, to a hydroxytyrosol content that is easily up to 10%, and that can reach 20%, 35% and even 40% by weight of hydroxytyrosol in the concentrated liquid product (i.e. extract).

In a further step of the invention process, the liquid products obtained by the previously discussed steps are dried in dryer means 20, e.g. freeze-dryer, vacuum rotoevaporator or preferably by spray-dryer, to produce a solid final product. The final product characteristics will be different according to the starting product (A, B or C) that is dried, the purity of the dry product being within the range of 45% to 99% (HPLC at 280 nm).

This drying step is preferably carried out on liquid products B and C, after concentrating them as above disclosed. The drying step can advantageously make use of carriers suitable for the final use of the dry product; suitable carriers are e.g. maltodextrines, lactose, lecithins, caseinates etcetera.

Suitable drying techniques are known in the art and comprise spray drying (usually with the use of carriers), freeze-drying and water evaporation under vacuum. The resulting products will have a hydroxytyrosol content of 0.5% to 10% and up to 20% (w/w) if a carrier is used, the hydroxytyrosol content can reach up to about 95% (w/w) if no carrier is used. It should be noticed that the invention process provides a purified liquid product (B and especially C) that is so pure that it can be evaporated to a dry powder even without carriers, this being not possible with known techniques.

The invention will now be further disclosed with reference to the following non-limiting examples.

Example 1

Hydroxytyrosol Extraction from Olive Waste (Orujillo), Purification of the Water Phase 250 g of a sample of dry olive waste, orujillo, are mixed with 838 ml of demineralized water and 16.7 g of sulphuric acid (98%). The obtained mixture is kept in autoclave for 30 minutes at 121° C. After that, the aqueous phase is separated from the solid residue, by filtering on a filter. The solid phase, retained on the filter, is washed with 310 ml of demineralized water, and the water coming from this washing operation is collected with the aqueous phase previously recovered. The aqueous phase, approximately 860 ml, is then centrifuge refined to eliminate solid particles passed through the filter. After solid elimination, 835 ml of crude aqueous extract, containing 1.41 g of hydroxytyrosol, with a HPLC purity of 47.5%, are obtained.

Example 2

Ion Exchange Hydroxytyrosol Purification

A sample of 835 ml of crude aqueous extract containing 1.41 g of hydroxytyrosol obtained according to Example 1, is loaded on a column containing a ion exchange resin of the anionic type, previously activated by means of acetate cycle. For example, Diaion WA10 may be used. The liquid phase recovered at the end of the column, does not contain any hydroxytyrosol, which is instead continuously eluted with demineralised water until at least 90% of the initially charged hydroxytyrosol is recovered. The eluted phase contains approximately 1.27 g of hydroxytyrosol with an HPLC purity of about 80.85%.

Example 3

Ion Exchange and Adsorption Hydroxytyrosol Purification

A sample of 835 ml of crude aqueous extract containing 1.41 g of hydroxytyrosol obtained according to Example 1, is loaded on a column containing an ion exchange resin of the anionic type, previously activated by means of acetate cycle. For example, IRA-67 may be used. The liquid phase recovered at the end of the column, does not contain any hydroxytyrosol, which is instead continuously eluted with demineralised water until at least 90% of the initially charged hydroxytyrosol is recovered.

The eluted phase coming from the first column, is charged on a column containing an adsorption resin. For example, resin XAD-1180 may be used. The liquid phase recovered at the end of the column, does not contain any hydroxytyrosol. Then, hydroxytyrosol is eluted from the resin with demineralised water until at least 90% of the initially charged hydroxytyrosol is recovered.

The eluted phase contains approximately 1.14 g of hydroxytyrosol with an HPLC purity of about 95.72%.

Example 4

Concentration of Hydroxytyrosol Crude Extract Enriched by Evaporation

The aqueous phase obtained in Example 1 before the centrifugation step, approximately 860 ml, is concentrated by evaporation in order to reach a final volume of about 193 ml. The aqueous phase is then centrifuge refined to eliminate solid particles passed through the filter. After solid elimination, 160 ml of crude aqueous extract, containing 1.41 g of hydroxytyrosol, with a HPLC purity of 47.5%, are obtained.

Example 5

Concentration of Hydroxytyrosol Ion Exchange Purified Extract Enriched by Reverse Osmosis A sample of 80 l of crude aqueous extract containing 150 g of hydroxytyrosol obtained in a pilot plant according to Example 2, is concentrated using a reverse osmosis pilot plant, equipped with a 2.5 $m^2$ polymeric membrane, in order to reduce the volume to 10 l of concentrate product. A 0.3 $m^2$ membrane made of the same material is then used in order to obtain an hydroxytyrosol concentrate containing 10.8% of hydroxytyrosol with an HPLC purity of 80.53%.

Example 6

Concentration of Hydroxytyrosol Ion Exchange and Adsorption Purified Extract by Reverse Osmosis A sample of 546 l of crude aqueous extract containing 135 g of hydroxytyrosol obtained in a pilot plant according to Example 3, is concentrated using a reverse osmosis pilot plant, equipped with a 2.5 $m^2$ polymeric membrane, in order to reduce the volume to 10 l of concentrate product. A 0.3 $m^2$ membrane made of the same material is then used, in order to obtain an hydroxytyrosol concentrate containing 12.20% of hydroxytyrosol with an HPLC purity of 95.27%.

Example 7

Spray-Drying of the Crude Extract Enriched in Hydroxytyrosol Without Any Purification A sample of 442 ml of crude aqueous extract containing 1.02 g of hydroxytyrosol obtained according to Example 1, is mixed with 100 g of maltodextrin, until maltodextrin was completely dissolved. For example, equivalent 10 dextrose potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 95 g of a brown powder, with a moisture of 6.85% (Karl Fischer) and a hydroxytyrosol richness of 0.98%, are obtained.

Example 8

Spray-Drying of the Partially Purified Aqueous Extract Enriched in Hydroxytyrosol A sample of 290 ml of aqueous extract containing 0.38 g of hydroxytyrosol obtained according to Example 2 and subsequently concentrated by reverse osmosis is mixed with 50 g of maltodextrin until maltodextrin was completely dissolved. For example, equivalent 10 dextrose potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 48.25 g of a greyish powder, with a moisture of 6.72% (Karl Fischer) and a hydroxytyrosol richness of 0.71%, are obtained.

Example 9

Spray-Drying of the Purified Aqueous Extract Enriched in Hydroxytyrosol

A sample of 188 ml of purified aqueous extract containing 0.29 g of hydroxytyrosol obtained according to Example 3, and subsequently concentrated by reverse osmosis, is slowly stirred with 28.5 g of maltodextrin. For example, equivalent 10 dextrose potato maltodextrin may be used. A peristaltic pump is used to feed the spray-dryer, which is previously equilibrated with an inlet air temperature of 175° C. The feeding speed is adjusted in order to obtain an outlet air temperature which is less than 100° C. 27.1 g of a white powder, with a moisture of 5.45% (Karl Fischer) and a hydroxytyrosol richness of 0.97%, are obtained.

Example 10

Preparation of a Highly Rich Hydroxytyrosol Powder

A sample of 1750 l of aqueous extract containing 432 g of hydroxytyrosol obtained, according to Example 3, in a pilot plant is concentrated according to Example 6, to obtain an hydroxytyrosol concentrate containing 39.04% of hydroxytyrosol with an HPLC purity of 95.60%. The concentrated solution is used to feed the spray-dryer, which is previously equilibrated with an inlet air temperature of 150° C. The feeding speed is adjusted in order to obtain an outlet air temperature less than 100° C. 375.84 g of a light brown powder, with a moisture of 4.35% (Karl Fischer) and a hydroxytyrosol richness of 94.74%, are obtained.

Example 11

Olive Extracts Production from Olives Fruits

25 Kg of a sample of olives fruits are mixed with 50 L of demineralised water. The obtained mixture is blended for a few minutes, and then 636 g of sulphuric acid (98%) were added. The obtained mixture is kept in autoclave for 30 minutes at 121° C. After that, the aqueous phase is separated from the solid olive residue, by filtering on a filter. The solid phase, retained on the filter, is washed with 12.5 L of demineralised water, and the water coming from this washing operation is collected with the aqueous phase previously recovered. The aqueous phase, approximately 63 L, is then filtered trough a Kieselguhr filter pre-coated with a Celite™ 500 diatomaceous earth to eliminate the extracted oil. The oil-free aqueous phase, about 56 L, is then centrifuge refined to eliminate solid particles passed through the Kieselguhr filter After solid elimination, 52 L of crude aqueous extract, containing 141 g of hydroxytyrosol, with a HPLC purity of 50.5%, are obtained.

Then, crude aqueous extract, is loaded on a column containing an ion exchange resin of the anionic type, previously activated by means of acetate cycle. For example, IRA-67 may be used. The liquid phase recovered at the end of the column, does not contain any hydroxytyrosol, which is instead continuously eluted with demineralised water until at least 90% of the initially charged hydroxytyrosol is recovered.

The eluted phase coming from the first column is charged on a column containing an adsorption resin. For example, resin XAD-1180 may be used. The liquid phase recovered at the end of the column, does not contain any hydroxytyrosol. Then, hydroxytyrosol is eluted from the resin with demineralised water until at least 90% of the initially charged hydroxytyrosol is recovered.

The eluted phase contains approximately 114 g of hydroxytyrosol with an HPLC purity of about 96.7%.

Then, a 461 L fraction of purified extract containing 114 g of hydroxytyrosol obtained in a pilot plant is concentrated using a reverse osmosis pilot plant, equipped with a 2.5 m$^2$ polymeric membrane, in order to reduce the volume to 10 l of concentrate product. A 0.35 m$^2$ membrane made of the same material is then used, in order to obtain a hydroxytyrosol concentrate containing 3.5% of hydroxytyrosol. Finally the RO concentrate is rotaevaporated at 78° C. under a vacuum pressure of 245 mbar to allow about 10 times concentration of the olive fruit extract in liquid form reaching a final concentration of 37.2% (w/w) with an HPLC purity of 93.3%.

Example 12

Preparation of Olive Fruit Extract Powder by Spray-Drying

A sample of 260 ml of purified olive extract in liquid form containing 19.5 g of hydroxytyrosol obtained according to Example 11, is slowly stirred with 58 g of maltodextrin previously dissolved in 260 ml of demineralised water. For example, potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 76 g of a white powder, with a moisture of 5.4% (Karl Fischer) and a hydroxytyrosol richness of 21.9% (w/w), are obtained.

Example 13

Hydroxytyrosol Extraction from Three Phases Pomaces (Defatted Orujo), Purification of the Aqueous Phase 475.5 g of a sample of three phases pomace with a humidity of 60.55%, are mixed with 800 ml of demineralized water and 26.36 g of sulphuric acid (98%). The obtained mixture is kept in autoclave for 30 minutes at 121° C. After that, the aqueous phase is separated from the solid residue, by filtering on a 600 micron polypropylene filter. The filtered aqueous phase, approximately 795 ml, is concentrated by evaporation in order to reach a final volume of about 343.8 ml. The aqueous phase is then centrifuge refined to eliminate solid particles passed through the filter. After solids elimination, 275 ml of crude aqueous extract, containing 0.97 g of hydroxytyrosol, with a HPLC purity of 54%, are obtained.

Example 14

Ion Exchange and Adsorption Purification of Hydroxytyrosol Deriving from Three Phases Pomace (Defatted Orujo)

A sample of 275 ml of crude aqueous extract containing 0.97 g of hydroxytyrosol obtained according to Example 13, is loaded on a column containing an ion exchange resin of the anionic kind, previously activated by means of acetate cycle. For example, Diaion WA10 resin may be used. The liquid phase recovered at the end of the column, does not contain any hydroxytyrosol, which is instead continuously eluted with demineralised water until at least 90% of the initially charged hydroxytyrosol is recovered.

The eluted phase coming from the first column is loaded on a column containing an adsorption resin. For example, resin Diaion HP20 may be used. The liquid phase recovered at the end of the column, does not contain any hydroxytyrosol. Then, hydroxytyrosol is eluted from the resin with demineralised water until at least 90% of the initially charged hydroxytyrosol is recovered.

The eluted phase contains approximately 0.80 g of hydroxytyrosol with an HPLC purity which is higher than 95%.

As previously mentioned, the process of the invention provides for preparing an extract containing hydroxytyrosol starting from olives and/or pomaces without making use of organic polar solvents. The products obtained according to this process, both the final products and the intermediate products, are therefore free from organic polar solvents. The products are also substantially free from sugars and salts. This is possible by the combined use of the claimed hydrolysis conditions and purification procedure.

The final product, because of its high purity and high hydroxytyrosol content, in particular a solid hydroxytyrosol extract free from carriers and organic solvents is highly suitable for use in the food industry, and in cosmetic and pharmaceutical industries.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The invention claimed is:

1. A process of producing an extract containing hydroxytyrosol from a starting material selected from olives and/or pomaces residues of olives after an extraction of olive oil, said process including acid hydrolysis of said starting material and purification of the resulting solution, the process comprising:
   a) carrying out said acid hydrolysis of said starting material in water at a temperature within the range of 70° C. to 140° C., at a pressure within the range of atmospheric pressure to 20 psi above the atmospheric pressure and at a pH within the range of 1.0 to 6.0;
   b) removing suspended solids from the hydrolysis water solution of step a) to obtain a clarified aqueous solution;
   c) loading a product (A) obtained from step b) in a chromatographic column of a resin selected from acid activated anion exchange resins to retain hydroxytyrosol,
   d) eluting the products retained over said chromatographic resin with water;
   e) loading a solution (B) obtained from step d) in a second chromatographic column of a resin selected from adsorbent non-ionic resins, to retain hydroxytyrosol;
   f) eluting the products retained over said second chromatographic resin with water.

2. A process according to claim 1, wherein said hydrolysis is carried out in a continuous sterilization system and the hydrolysis temperature is within the range of 110° C. to 130° C. and at a pressure that is 10 to 20 psi above atmospheric pressure.

3. A process according to claim 1, wherein the duration of said hydrolysis step is within the range of 15 to 45 minutes.

4. A process according to claim 2, wherein the hydrolysis temperature is within the range of 118 to 126° C.

5. A process according to claim 1, further comprising reverse osmosis concentration of the solution (B) obtained from step d) or of a solution (C) obtained from step f).

6. A process according to claim 1, further comprising water removal
   i) from the solution (B) obtained from step d) or ii) from a solution (C) obtained from step f) until the product is in a solid form.

7. A process according to claim 1, wherein oil is removed from the starting material or from the water solution obtained from step b).

8. An extract, as obtainable through a process according to claim 1, wherein said extract is free from organic solvents and free from sugars and salts, and in that the content of hydroxytyrosol in said extract is at least 10% (w/w) and the hydroxytyrosol purity is at least 45% (by HPLC 280 nm).

9. An extract according to claim 8, wherein the extract is liquid and has the hydroxytyrosol content of at least 30% (w/w) and the purity of at least 90% (by HPLC 280 nm).

10. An extract according to claim 8, wherein the extract is solid and wherein the content of hydroxytyrosol in said extract is at least 10% (w/w) and the hydroxytyrosol purity is at least 45% (by HPLC 280 nm).

11. A solid extract according to claim 10, wherein the extract has the hydroxytyrosol content of at least 40% (w/w) and the purity of at least 90% (by HPLC 280 nm).

12. An extract according to claim 8, as obtainable from step d) and having the purity of at least 75% (by HPLC 280 nm).

13. An extract, as obtainable through a process according to claim 1, wherein said extract is free from organic polar solvents and has been isolated from sugars and salts, and wherein the content of hydroxytyrosol in said extract is at least 10% (w/w) and the hydroxytyrosol purity is at least 40% (by HPLC 280 nm).

* * * * *